United States Patent [19]

Lindmayer et al.

[11] Patent Number: 5,028,793
[45] Date of Patent: Jul. 2, 1991

[54] IMAGING SCREEN FOR ELECTROPHORESIS APPLICATIONS

[75] Inventors: Joseph Lindmayer, Potomac; Charles Y. Wrigley, Ijamsville, both of Md.; George M. Storti, Washington, D.C.

[73] Assignee: Quantex Corporation, Rockville, Md.

[21] Appl. No.: 383,534

[22] Filed: Jul. 24, 1989

Related U.S. Application Data

[63] Continuation-in-part of Ser. No. 203,324, Jun. 8, 1988, Pat. No. 4,983,834, which is a continuation-in-part of Ser. No. 85,465, Aug. 14, 1987, Pat. No. 4,812,660, and a continuation-in-part of Ser. No. 34,333, Mar. 3, 1987, Pat. No. 4,822,520.

[51] Int. Cl.$^5$ ............................................. G03B 42/00
[52] U.S. Cl. .............................. 250/484.1; 250/327.2; 250/363.04; 364/413.13
[58] Field of Search ............ 250/327.2, 363.03, 363.04, 250/484.1; 364/413.13, 413.23, 413.26

[56] References Cited

U.S. PATENT DOCUMENTS

| | | | |
|---|---|---|---|
| 4,617,468 | 10/1986 | Shiraishi et al. | 250/484.1 |
| 4,734,581 | 3/1988 | Hashiue | 250/327.2 |
| 4,839,092 | 6/1989 | Lindmayer | 252/301.45 |
| 4,855,603 | 8/1987 | Lindmayer | 250/484.1 |
| 4,874,492 | 10/1989 | Mackay | 204/182.8 |

FOREIGN PATENT DOCUMENTS

| | | | |
|---|---|---|---|
| 0113672 | 7/1984 | European Pat. Off. | 250/327.2 |
| 0113676 | 7/1984 | European Pat. Off. | 250/327.2 |
| 0113677 | 7/1984 | European Pat. Off. | 250/327.2 |
| 0126218 | 11/1984 | European Pat. Off. | |
| 0159523 | 10/1985 | European Pat. Off. | |

Primary Examiner—Constantine Hannaher
Assistant Examiner—Jacob M. Eisenberg
Attorney, Agent, or Firm—Ostrolenk, Faber, Gerb & Soffen

[57] ABSTRACT

An imaging screen for detecting and storing information corresponding to the pattern of emission from an electrophoresis gel containing radioactively labelled, dye-tagged or chemiluminescent labelled DNA, RNA, or protein fragments. The imaging screen is coated with an electron trapping material which releasably stores energy from the impingement of the emission from the electrophoresis gel in the form of energy corresponding the pattern and flux of the emission. When subjected to optical energy of a first wavelength, the electron trapping material releases the stored energy in the form of optical energy of a second wavelength corresponding the flux and pattern of the emission from the electrophoresis gel. The released optical energy of a second wavelength is then detected and coverted to electrical signals representative of the flux and pattern of emission from the electrophoresis gel.

20 Claims, 3 Drawing Sheets

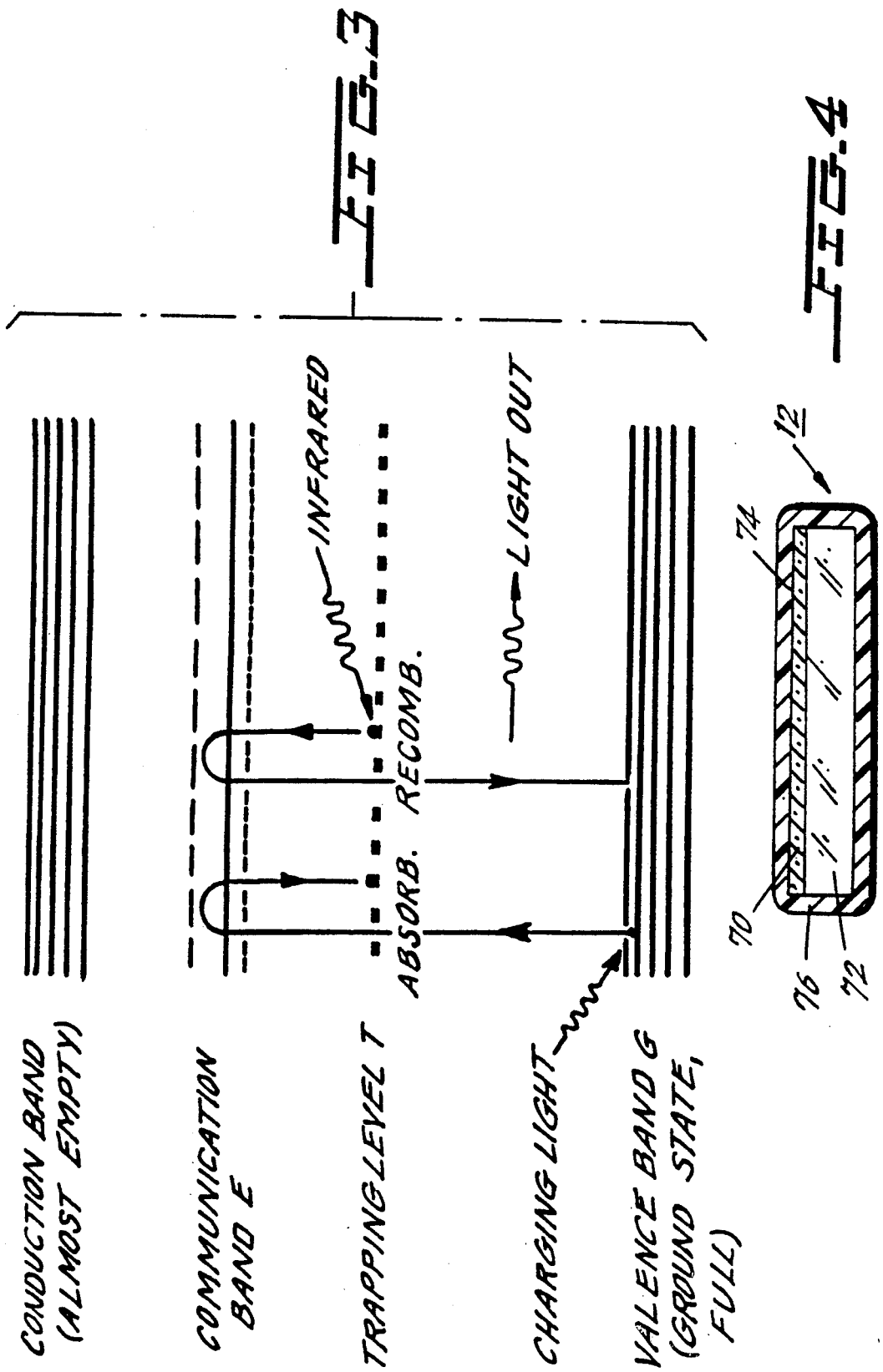

IMAGING SCREEN FOR ELECTROPHORESIS APPLICATIONS

This application is a continuation-in-part application of commonly assigned U.S. patent application Ser. No. 203,324, filed June 8, 1988, entitled LARGE AREA PARTICLE DETECTOR SYSTEM, now U.S. Pat. No. 4,983,834 which is a continuation-in-part of U.S. patent application Ser. No. 085,465, filed Aug. 14, 1987, now U.S. Pat. No. 4,812,660 and U.S. patent application Ser. No. 034,333, filed Mar. 3, 1987, now U.S. Pat. No. 4,822,520.

The assignee of the instant application is also the assignee of the following related United States patents and patent applications: U.S. Pat. No. 4,822,520, entitled PHOTOLUMINESCENT MATERIALS FOR OUTPUTTING BLUE-GREEN LIGHT; U.S. Pat. No. 4,839,092, entitled PHOTOLUMINESCENT MATERIALS FOR OUTPUTTING ORANGE LIGHT AND A PROCESS FOR MAKING SAME; U.S. Pat. No. 4,812,660, entitled PHOTOLUMINESCENT MATERIALS FOR OUTPUTTING YELLOW-GREEN LIGHT; U.S. Pat. No. 4,842,960, entitled HIGH EFFICIENCY PHOTOLUMINESCENT MATERIAL FOR OPTICAL UPCONVERSION; U.S. Pat. No. 4,855,603, entitled PHOTOLUMINESCENT MATERIALS FOR RADIOGRAPHY; and U.S. Pat. No. 4,879,186, entitled PHOTOLUMINESCENT MATERIALS FOR OUTPUTTING REDDISH-ORANGE LIGHT.

The disclosure of each of those related patent applications is incorporated by reference herein.

BACKGROUND OF THE INVENTION

1. Field of the Invention

The present invention relates generally to an imaging screen for electrophoresis applications and, more particularly, to an imaging screen for detecting and recording the impingement of beta particles or visible light emitted from electrophoresis gels.

2. Description of the Related Art

In order to sequence deoxyribonucleic acid (DNA), it is necessary to chemically treat and label DNA fragments prior to performing electrophoresis. Specifically terminated fragments of the DNA are placed in wells in a gel and an electric field applied, resulting in the motion along well-defined lanes in the gel. Depending on the length of the fragments and the time for performing the electrophoresis, they will travel more or less far along the lanes. The result of the electrophoresis operation is a pattern of bands of DNA fragments.

If the fragments have been labelled with a beta particle emitter, it is possible to obtain a two-dimensional map of the pattern by placing X-ray film in relatively intimate contact to the gel. The X-ray film is somewhat sensitive to the beta particle radiation, and generally after long exposure will record the pattern. Unfortunately, such a procedure typically requires a time period on the order of days for the film to register a sufficient number of emitted beta particles to provide an accurate representation of the pattern of bands.

Another drawback to this method is associated with the properties of X-ray film. Because of its limited dynamic range, and the complexity of obtaining quantitative information using such film, efforts have been undertaken to develop simpler, speedier and more accurate methodologies to detect radioactively labelled DNA fragments in electrophoresis gels.

Four beta emitters are typically employed for tagging DNA fragments—i.e., $^{32}P$, $^{35}S$, $^{14}C$, and $^{3}H$. The beta particles end point energies are 1.71 MeV, 168 keV, 156 keV, and 18.6 keV, respectively. The electron ranges vary greatly, with $^{32}P$ having the longest range, and $^{3}H$ having the shortest range.

Recently developed devices for obtaining quantitative information from radioactively labelled DNA, RNA or protein fragments in electrophoresis gels generally utilize two coincident grids which sense the beta emissions from the gels. Such a device is marketed as the Betascope 603 Blot Analyzer. That device can perform an analysis of the emitted beta particles in a number of hours. However, the Betascope device, and similar such devices, cannot readily detect the shorter range and lower energy beta particles. In addition, its spatial resolution is poor.

Fuji has developed a BaFBr imaging screen system which can work with $^{32}P$, $_{35}S$, and $^{14}C$, but is at least 1-2 orders of magnitude slower then the Betascope Blot Analyzer in processing the information contained in the radioactively labelled DNA, RNA or protein carrying electrophoresis gel.

Accordingly, there is a need for a simple, speedy and accurate methodology for detecting radioactive tracers emitted from electrophoresis gels. It would be additionally advantageous if such methodology could also be utilized to detect dye-tagged and chemiluminescent tracers which emit visible light, which the Fuji BaFBr system cannot detect.

SUMMARY OF THE INVENTION

The present invention achieves the above-described objectives by providing an imaging screen coated with a light stimulable storage phosphor appropriately doped for optimal sensitivity to ionizing radiation or visible light. The phosphor-coated screen is placed adjacent to the electrophoresis gel, so that the phosphor is charged with energy corresponding to the flux and pattern of the emission from the gel. Light of a first wavelength is then applied to the phosphor to stimulate the phosphor to release the stored energy in the form of light of a second wavelength. The light released from the phosphor is then detected and converted to electrical signals representative of the flux and pattern of the emission from the electrophoresis gel.

The storage phosphor is preferably a strontium sulfide or calcium sulfide based material doped with samarium and a cerium compound for optimum detection of the beta particle emission from a radioactively labelled biological fragment, or doped with samarium and a europium compound in place of or in addition to a cerium compound for optimum detection of the visible light emission from a dye-tagged or chemiluminescent labelled biological fragment.

These and other features and advantages of the present invention will become apparent when the following text is read in conjunction with the accompanying drawing.

BRIEF DESCRIPTION OF THE DRAWING

FIG. 3 is a schematic illustrating the principle of operation of the electron trapping material of the present invention; and FIG. 4 shows a cross-section of the imaging screen of the present invention.

DETAILED DESCRIPTION OF THE PREFERRED EMBODIMENT

Figure 1:
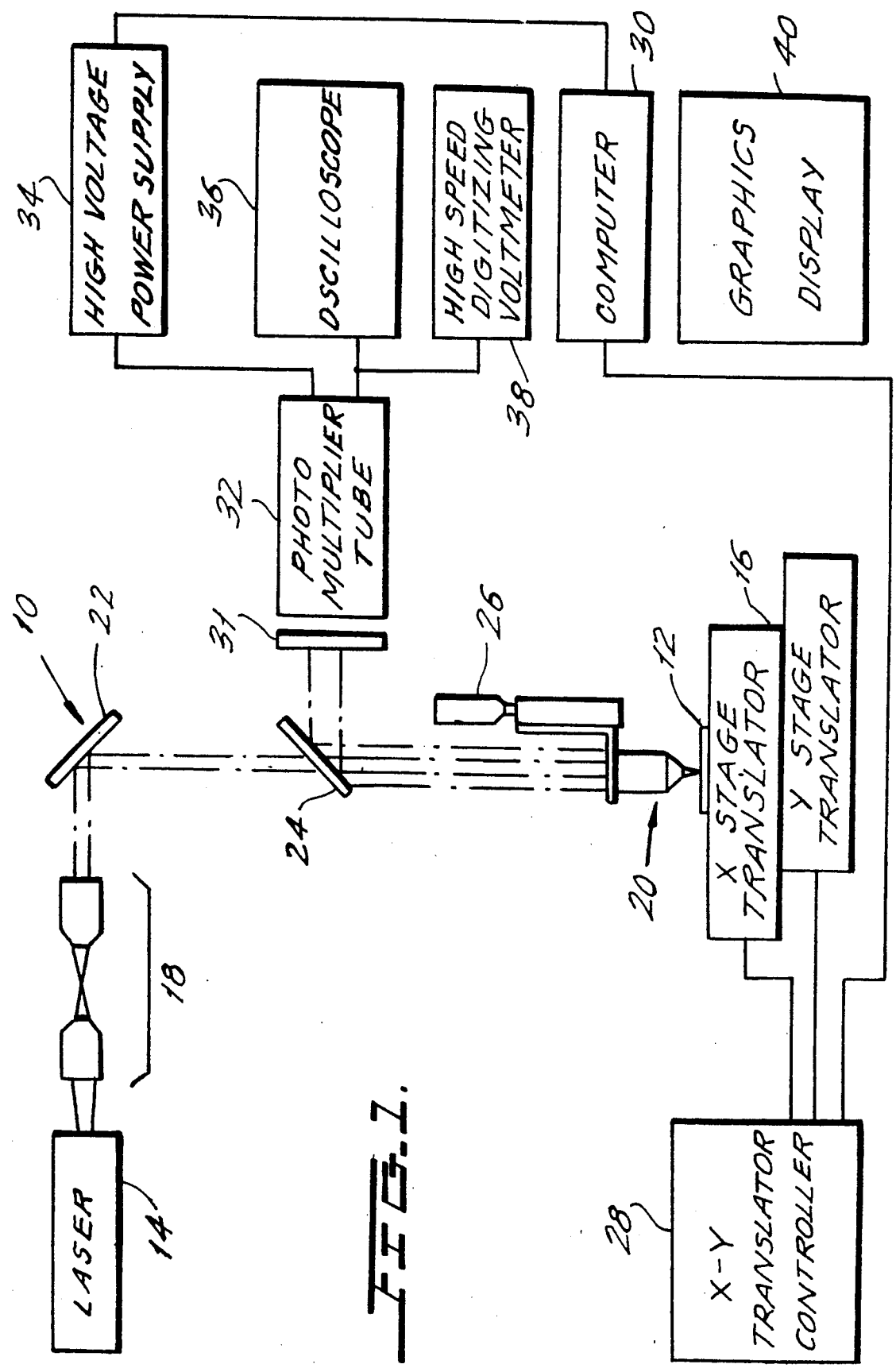
FIG. 1 is an overall block diagram of the system in which the imaging screen is scanned in a pixel-by-pixel manner and the light output from the screen is detected by a photomultiplier.

Referring now in detail to the drawing, there is illustrated in a detection system 10 for use with an imaging screen 12, fabricated as will be described later herein. Screen 12 has been placed on an electrophoresis gel containing radioactively labelled, dye-tagged, or chemiluminescent labelled DNA, RNA or other protein fragments for exposure. The beta particles or visible light emitted by the labelled or tagged fragments impinge upon the surface of the imaging screen which is coated with an electron trapping material as described later. A laser 14 is utilized to scan the surface of the imaging screen by impinging a laser beam onto the electron trapping material in a row-by-row and column-by-column manner. The imaging screen in mounted on an x-y stepping stage 16 for that purpose.

Laser 14 is preferably a 50 milliwatt Nd:Yag laser with an output having a wavelength centered about 1064 nm. Alternatively, a laser diode, with an output centered about 860 nm may be used in the present invention. In the operation of the device, laser 14 reads out the information stored in the electron trapping material. When it is desired to "erase" the impingement pattern stored in the electron trapping material, broad area infrared light produced by a filtered light source can be employed for the erasure. The output of laser 14 is controlled by a constant current power supply (not shown). The output from laser 14 is collimated by collimating optics 18 and then reflected by a IR mirror 22 through a cold mirror 24 and into a 20x microscope objective 20. A micrometer 26 is used to adjust the image of the laser beam down to less than a 20 micron spot on imaging screen 12.

As mentioned previously, imaging screen 12 is mounted on a x-y stepping stage 16, such as that available from Aerotech, for serial scan-readout. An x-y translator controller 28, under command of a microcomputer 30, moves the x-y stepping stage 16 so that the trapped electron population is scanned by laser 14 in a pixel-by-pixel manner. The release of trapped electrons in the electron trapping material results in the emission of visible light, which travels back up through microscope objective 20 and is deflected by cold mirror 24 through a short pass filter 31 and into a visible light detector 32, preferably a photomultiplier tube such as Hamamatsu Model R268.

Alternatively, visible light detector 32 can be a solid state image capture array, such as a CID or CCD, e.g., a Fairchild CID 2250 camera chip. In this case, as shown in FIG. 2, the entire surface of imaging screen 12 is illuminated with infrared light for read out; i.e. scanning is not necessary.

Figure 2:
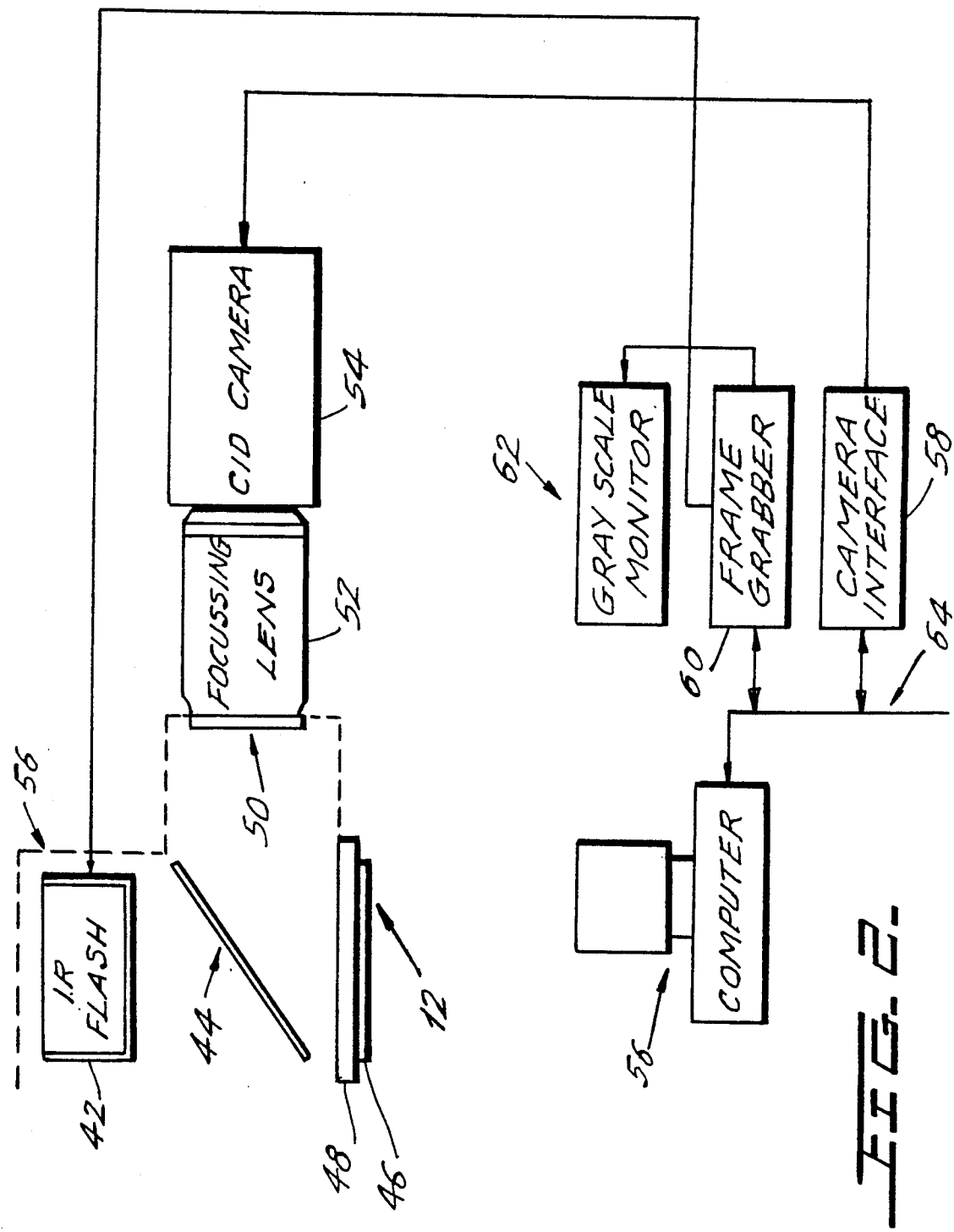
FIG. 2 is an overall block diagram of the system in which the light detector is a CID camera and the entire surface of the imaging screen is illuminated with infrared light for readout.

In the preferred arrangement shown in FIG. 2, infrared illumination is provided by an infrared flash 42. The infrared light passes through a cold mirror 44 and onto the imaging screen 12. Imaging screen 12 may be mounted in the film holder 46 of a camera back 48. The visible light emitted from the electron trapping material is reflected off cold mirror 44 and passes through an optical filter 50 and a lens 52 before entering a CID camera 54. Optical filter 50 is of the type that transmits visible light and blocks infrared light. Lens 52 is a 55 mm f 2.8 lens which focuses an image of imaging screen 12 onto CID camera 54. A light-tight enclosure 56 prevents external light from entering the optical portion of the system.

The system of FIG. 2 is controlled by a microcomputer 56. Specifically, microcomputer 56 controls CID camera 54 via a camera interface 58. Each frame of video information corresponding to the image received by CID camera 54 is collected by a frame grabber 60 (under control of microcomputer 56) and displayed on a gray scale video monitor 62. Frame grabber 60 also generates a signal for triggering infrared flash 42. Digital communication between microcomputer 56, camera interface 58 and frame grabber 62 occurs over a computer bus 64.

If a photomultiplier is used the visible light detector as shown in FIG. 1, it is powered by a high voltage power supply 34, and the output of the photomultiplier (an electrical signal proportional to the detected visible light input) is fed to an oscilloscope 36 (for visual display) and to a high speed digitizing voltmeter 38 (for A/D conversion). The digital output of digitizing voltmeter 38 is fed into microcomputer 30 for processing and conversion into an image which is displayed on graphics display 40.

As will be apparent to those skilled in the art, the above-described system and its components are merely the preferred embodiment of the invention. Thus, many other types of infrared light sources, scanning systems and visible light detectors may be utilized to stimulate the charged electron trapping material in imaging screen 12 and to detect the visible light emitted therefrom. The preferred embodiment described above is capable of resolving a "pixel" size of 200 micrometers or smaller on the surface of imaging screen 12.

The electron trapping material and the fabrication of imaging screen 12 will now be described.

The electron trapping material utilized in the present invention is a novel photoluminescent material which can be "charged" by the radiation or visible light to be measured; upon such energetic exposure, electrons in the material are raised to a higher energy state where they are "trapped" and stay indefinitely. When low energy photons (such as infrared) impinge upon the material, the stored electrons are released from their traps, and, upon falling to a lower energy level, emit visible light which can be detected and measured.

FIG. 3 shows the principles of operation of the electron trapping material used in the present invention. The basic crystalline photoluminescent material used has a valence band G full of electrons at a ground state. The material is subjected to radiation or visible light which functions to energize certain electrons in the valence band G. An electron shown on the left is originally in a valence band G and is subjected to charging radiation or visible light. The electron absorbs a beta particle or photon raising its energy level to a communication band E where communication takes place with other energized electrons resulting in transitions. Upon removal of the energizing radiation or light, the electron may drop back to a trapping level T or back to the valence band G depending upon the composition of the material and available trapping sites. The electron, if in the trapping level T, will remain isolated from other electrons and trapped until sufficient additional energy is provided to the electron to raise its energy back up to the communication band E where it may interact with other electrons and undergo recombination causing it to move back to the valence band G and output a photon of visible light in the process.

The number of trapping sites, the depth of the traps and the probability of transitions occurring in the communication band are all dependent upon the composition of the photoluminescent material used.

The electron trapping material is formed of a strontium sulfide and/or calcium sulfide base combined with samarium metal or a samarium compound as a first dopant and either a europium compound or a cerium compound, or both, as a second dopant. Lithium fluoride is preferably added as a flux to provide fusibility, and barium sulfate can be used to improve the brightness of light output from the material.

In the case of analyzing a radioactively labelled biological fragments, a cerium compound is used as a second dopant to provide an electron trapping material with improved sensitivity to beta particles. Examples of such electron trapping materials are disclosed in U.S. Pat. No. 4,822,520, U.S. Pat. No. 4,855,603 and U.S. Pat. No. 4,812,660, the disclosures of which are herein incorporated by reference. The electron trapping materials of the first two patents emit blue-green light, while the material of the third patent emits a yellow-green light.

In the case of analyzing a dye-tagged or chemiluminescent labelled electrophoresis gel, it is preferable to use a europium compound as the second dopant to provide an electron trapping material with a brighter output. Examples of europium doped electron trapping materials are disclosed in U.S. Pat. No. 4,839,092, U.S. Pat. No. 4,842,960 and U.S. Pat. No. 4,879,186 the disclosures of which are herein incorporated by reference. The electron trapping materials of the first two patents emit orange light, while the material of the third patent emits a reddish-orange light.

The cerium and europium doped electron trapping materials described in the above-identified patents have electron traps on the order of approximately 1.0 eV.

The process for making thick and thin film versions of the various cerium and europium doped electron trapping material is described in detail in the referenced patents and is not repeated here. Either a thick or thin film of the electron trapping material may be applied to a substrate (e.g. vitreous quartz) to form the detector screen of the present invention. The advantage of the thick film version (having a thickness on the order of hundreds of microns) is that all incoming flux, e.g. beta particles, is absorbed by the material and stored as energy in the form of trapped electrons. The advantage of the thin film version (having a thickness on the order of microns) is that very low energy beta particles such as from $^3H$ can be detected with a higher signal to noise ratio.

If higher energy radioactive particles are to be detected (e.g. from $^{32}P$, $^{35}S$, or $^{14}C$), the electron trapping material is fused at a high temperature, ground, either attached or reheated at a lower temperature and then mixed with a binder and dispersed onto the substrate.

The thin film version can be used where the flux emitted from the electrophoresis gel is of very low energy. Generally, the thin film version is prepared by physical vapor deposition of the fused material directly onto the substrate. The patents referenced above provide a more detailed discussion of the thick and thin film deposition techniques.

FIG. 4 shows a cross-sectional view of an imaging screen 12 in which a film of electron trapping material 70 is disposed upon a substrate 72. Any of a number of known materials having suitable properties may be used for the substrate 72. Some examples of substrates that may be useful are: sapphire, alumina, other ceramics, quartz, fiber optic faceplates, other glasses, metals such as aluminum, various organic polymers, and polycarbonates. The material 70 establishes a planar surface 74 on substrate 72. An optional transparent coating 76 may encapsulate the material 70 and substrate 72.

Although the present invention has been described in relation to particular embodiments thereof, many other variations and modifications and other uses will become apparent to those skilled in the art. It is preferred, therefore, that the present invention be limited not by the specific disclosure herein but only by the appended claims.

What is claimed is:

1. Apparatus for obtaining information from an electrophoresis gel containing a sample of radioactively labelled DNA, RNA or protein, comprising:

means for detecting and storing information corresponding to the impingement of a pattern of emission from said electrophoresis gel, comprising an imaging screen coated with an electron trapping material for releasably storing said information as energy corresponding to the flux and pattern of said emission, said electron trapping material comprising:

a base material comprising substantially strontium sulfide;

a first dopant of samarium provided in a quantity of between 70 to 300 parts per million by weight; and a second dopant of cerium oxide provided in a quantity of between 600 to 1500 parts per million by weight;

means for applying optical energy of a first wavelength to said electron trapping material for causing said electron trapping material to release optical energy of a second wavelength corresponding to said flux and pattern of said emission; and means for sensing said released optical energy of said second wavelength and for converting said released optical energy to electrical signals representative of said flux and pattern of said emission.

2. The apparatus of claim 1, further including means for applying erase optical energy to said means for detecting and storing information for erasing the information stored thereon.

3. The apparatus of claim 1, wherein said pattern of emission on said detector is accumulated over a period of time, effectively integrating the resulting stored pattern.

4. The apparatus of claim 1, wherein said emission comprises beta particles released from radioactively labelled DNA, RNA or protein in said electrophoresis gel.

5. The apparatus of claim 4, wherein said electron trapping material comprises a base material of an alkaline earth metal sulfide or a mixture of alkaline earth metal sulfides doped with samarium metal or a samarium compound and doped with a cerium compound.

6. The apparatus of claim 5, wherein said electron trapping material further comprises a fusable salt.

7. A method for obtaining data from an electrophoresis gel containing a sample of radioactively labelled DNA, RNA or protein, comprising the steps of:
placing said electrophoresis gel on an imaging screen coated with an electron trapping material for detecting and storing energy corresponding to flux and pattern of the emission from said electrophoresis gel, said electron trapping material comprising:
a base material comprising substantially strontium sulfide;
a first dopant of samarium provided in a quantity of between 70 to 300 parts per million by weight; and
a second dopant of cerium oxide provided in a quantity of between 600 to 1500 parts per million by weight; subjecting said electron trapping material to optical energy of first wavelength to cause said electron trapping material to release optical energy of a second wavelength corresponding to said flux and pattern of said emission; and
sensing said released optical energy of a second wavelength and converting said optical energy to electrical signals representative of said flux and pattern of said emission.

8. The method of claim 7, further including the step of applying erase optical energy to said electron trapping material for erasing the radiation pattern stored thereon.

9. The method of claim 7, wherein the depth of traps contained in said electron trapping material is about 1.0 eV.

10. Apparatus for obtaining information from an electrophoresis gel containing a sample of radioactively labelled DNA, RNA or protein, comprising:
means for detecting and storing information corresponding to the impingement of a pattern of emission from said electrophoresis gel, comprising an imaging screen coated with an electron trapping material for releasably storing said information as energy corresponding to the flux and pattern of said emission, said electron trapping material comprising:
a base material selected from the group of alkaline earth metal sulfides;
a first dopant of samarium;
a second dopant selected from the group of cerium oxide, cerium fluoride, cerium chloride, and cerium sulfide; and
a cesium halide; means for applying optical energy of a first wavelength to said electron trapping material for causing said electron trapping material to release optical energy of a second wavelength corresponding to said flux and pattern of said emission; and
means for sensing said released optical energy of said second wavelength and for converting said released optical energy to electrical signals representative of said flux and pattern of said emission.

11. Apparatus for obtaining information from an electrophoresis gel containing a sample of radioactively labelled DNA, RNA or protein, comprising:
means for detecting and storing information corresponding to the impingement of a pattern of emission from said electrophoresis gel, comprising an imaging screen coated with an electron trapping material for releasably storing said information as energy corresponding to the flux and pattern of said emission, said electron trapping material having a peak infrared sensitivity within the range of 1.12 or 1.22 microns and emitting in response to infrared radiation an output of yellow-green light, said electron trapping material comprising:
a base material comprising substantially calcium sulfide;
a first dopant of samarium provided in a quantity of between 50 and 300 parts per million by weight, and
a second dopant selected from the group of cerium oxide, cerium fluoride, cerium chloride, and cerium sulfide provided in a quantity between 200 to 1500 parts per million by weight;
means for applying optical energy of a first wavelength to said electron trapping material for causing said electron trapping material to release optical energy of a second wavelength corresponding to said flux and pattern of said emission; and
means for sensing said released optical energy of said second wavelength and for converting said released optical energy to electrical signals representative of said flux and pattern of said emission.

12. A method for obtaining data from an electrophoresis gel containing a sample of radioactively labelled DNA, RNA or protein, comprising the steps of:
placing said electrophoresis gel on an imaging screen coated with an electron trapping material for detecting and storing energy corresponding to flux and pattern of the emission from said electrophoresis gel, said electron trapping material, comprising:
a base material selected from the group of alkaline earth metal sulfides;
a first dopant of samarium;
a second dopant selected from the group of cerium oxide, cerium fluoride, cerium chloride, and cerium sulfide; and
a cesium halide; subjecting said electron trapping material to optical energy of first wavelength to cause said electron trapping material to release optical energy of a second wavelength corresponding to said flux and pattern of said emission; and
sensing said released optical energy of a second wavelength and converting said optical energy to electrical signals representative of said flux and pattern of said emission.

13. A method for obtaining data from an electrophoresis gel containing a sample of radioactively labelled DNA, RNA or protein, comprising the steps of:
placing said electrophoresis gel on an imaging screen coated with an electron trapping material for detecting and storing energy corresponding to flux and pattern of the emission from said electrophoresis gel, said electron trapping material having a peak infrared sensitivity within the range of 1.12 or 1.22 microns and emitting in response to infrared radiation an output of yellow-green light comprising:
a base material comprising substantially calcium sulfide;
a first dopant of samarium provided in a quantity of between 50 and 300 parts per million by weight, and
a second dopant selected from the group of cerium oxide, cerium fluoride, cerium chloride, and cerium sulfide provided in a quantity between 200 to 1500 parts per million by weight; subjecting said electron trapping material to optical energy of first wavelength to cause said electron trapping material to release optical energy of a second wavelength corresponding to said flux and pattern of said emission; and sensing said released optical energy of a second wavelength and converting said optical energy to electrical signals representative of said flux and pattern of said emission.

14. Apparatus for obtaining information from an electrophoresis gel containing a sample of dye-tagged, or chemiluminiscent labelled DNA, RNA or protein, comprising:

means for detecting and storing information corresponding to the impingement of a pattern of visible light emission from said electrophoresis gel, comprising an imaging screen coated with an electron trapping material for releasably storing said information as energy corresponding to the flux and pattern of said visible light emission;

means for applying optical energy of a first wavelength to said electron trapping material for causing said electron trapping material to release optical energy of a second wavelength corresponding to said flux and pattern of said visible light emission; and means for sensing said released optical energy of said second wavelength and for converting said released optical energy to electrical signals representative of said flux and pattern of said visible light emission.

15. The apparatus of claim 14, wherein said electron trapping material further comprises a base material of an alkaline earth metal sulfide or a mixture of alkaline earth metal sulfides doped with samarium metal or a samarium compound and doped with a europium compound.

16. The apparatus of claim 15, wherein said electron trapping material further comprises a fusible salt.

17. The apparatus of claim 14, further including means for applying erase optical energy to said means for detecting and storing information for erasing the information stored thereon.

18. An erasable imaging screen for use with electrophoresis gels containing a sample of dye-tagged or chemiluminiscent labelled DNA, RNA or protein, comprising:

a substrate carrying an electron trapping material for detecting and storing the pattern of visible light emission from said electrophoresis gel, said electron trapping material being capable of releasing optical energy of a first wavelength corresponding to the stored pattern of visible light emission when subjected to optical energy of a second wavelength.

19. A method for obtaining data from an electrophoresis gel containing a sample of dye-tagged or chemiluminscent labelled DNA, RNA or protein, comprising the steps of:

placing said electrophoresis gel on an imaging screen coated with an electron trapping material for detecting and storing energy corresponding to flux and pattern of the visible light emission from said electrophoresis gel;

subjecting said electron trapping material to optical energy of first wavelength to cause said electron trapping material to release optical energy of a second wavelength corresponding to said flux and pattern of said visible light emission; and sensing said released optical energy of a second wavelength and converting said optical energy to electrical signals representative of said flux and pattern of said emission.

20. The method of claim 19, further including the step of applying erase optical energy to said electron trapping material for erasing the radiation pattern stored thereon.

* * * * *